(12) United States Patent
Soslau

(10) Patent No.: US 6,841,354 B2
(45) Date of Patent: Jan. 11, 2005

(54) SCREENING ASSAY FOR ANTI-THROMBOTIC/ANTI-PLATELET ACTIVITY

(75) Inventor: Gerald Soslau, Feasterville, PA (US)

(73) Assignee: Philadelphia, Health & Education Corporation, Philadelphia, PA (US)

( * ) Notice: Subject to any disclaimer, the term of this patent is extended or adjusted under 35 U.S.C. 154(b) by 437 days.

(21) Appl. No.: 10/029,611

(22) Filed: Dec. 21, 2001

(65) Prior Publication Data

US 2002/0103107 A1 Aug. 1, 2002

Related U.S. Application Data

(60) Provisional application No. 60/257,067, filed on Dec. 21, 2000.

(51) Int. Cl.$^7$ .................................................. C12Q 1/56
(52) U.S. Cl. ........................................ 435/13; 435/214
(58) Field of Search ...................... 435/13, 214; 514/2, 514/12, 17; 530/324, 329, 380, 389.3

(56) References Cited

U.S. PATENT DOCUMENTS

| | | | |
|---|---|---|---|
| 5,892,014 A | * | 4/1999 | Coughlin et al. .......... 536/23.5 |
| 6,365,617 B1 | * | 4/2002 | McComsey et al. ........ 514/403 |
| 6,436,400 B1 | * | 8/2002 | Xu et al. .................. 424/143.1 |
| 6,544,750 B1 | * | 4/2003 | Schmaier et al. ............ 435/7.1 |

FOREIGN PATENT DOCUMENTS

| WO | WO 93/16712 | * | 9/1993 |
|---|---|---|---|
| WO | WO 99/43809 | * | 9/1999 |

OTHER PUBLICATIONS

Andrade–Gordon P. Design, Synthesis, and Biological Characterization of a Peptide Mimetic Antagonist for a Tethered Ligand Receoptor. PNAS 96(22) 12257–62, Oct. 1999.*

South V. Identification of Novel Peptide Antagonists for von Willebrand Factor Binding to the Platelet Glycoprotein 1b Receoptor from a Phage Epitope Library. Thrombosis and Haemostasis. 73(1) 144–150, 1995.*

Hllenberg M. Proteinase Activated Tethered Ligand Receptors. Bioactive Peptides in Drug Discovery and Design. vol. 22, pp. 265–274, 1999.*

Chang J.Y., "The structures and proteolytic specificities of autolysed human thrombin", Biochem. J. 1986 240:797–802.

Boissel et al., "Covalent Structures of $\beta$ and $\gamma$ Autolytic Derivatives of Human $\alpha$–Thrombin", J. Biol. Chem. 1984 259(9):5691–5697.

Jandrot–Perrus et al., "Cross–linking of $\alpha$ and $\gamma$–thrombin to distinct binding sites on human platelets", Eur. J. Biochem. 1988 174:359–367.

Smith et al., "Platelet Responses to Compound Interactions with Thrombin", Biochemistry 1999 38:8936–8947.

Ascenzi P., "Binding of Hirudin to Human $\alpha,\beta$ and $\gamma$–Thrombin", J. Mol. Biol. 1992 225:177–184.

Stone et al., "Basis for the Reduced Affinity of $\beta$T and $\delta$T Thrombin for Hirudin", Biochemistry 1991 30:3950–3955.

* cited by examiner

Primary Examiner—Ralph Gitomer
(74) Attorney, Agent, or Firm—Licata & Tyrrell P.C.

(57) ABSTRACT

A method for screening for anti-thrombotic/anti-platelet agents is provided where the method is based on inhibition of the GP Ib, PAR-1 and/or PAR-4 pathways by the potential anti-thrombotic/anti-platelet agent.

2 Claims, No Drawings

SCREENING ASSAY FOR ANTI-THROMBOTIC/ANTI-PLATELET ACTIVITY

This application claims the benefit of U.S. Provisional Application No. 60/257,067 filed Dec. 21, 2000.

BACKGROUND OF THE INVENTION

Despite advances in anti-platelet and anti-thrombotic treatment regimens, cardiovascular diseases remain the leading cause of death in the United States. Clinically employed anti-platelet and anti-thrombotic agents include heparin, aspirin, integrilin, and anti-GP IIb/IIIa antibodies (c7E3 Fab, abciximab, or ReoPro). α-Thrombin, generated at the site of vessel injury, is generally assumed to catalyze the hydrolysis of an N-terminal peptide from the human platelet 7-transmembrane thrombin receptor, protease activated receptor 1 (PAR-1), which initiates a cascade of molecular reactions leading to thrombus formation. Thrombin-induced activation of PAR-1, as for other agonist-activated platelet receptors, results in an outside-in signal transduced process followed by the alteration of the surface integrin, GP IIb/IIIa, by an inside-out signal (Schwartz, M. A. et al. 1995. *Ann. Rev. Cell Biol.* 11:549–599). The conformational change of GP IIb/IIIa leads to the $Ca^{+2}$-dependent binding of the bi-functional fibrinogen molecule (Bodary, S. C. et al. 1989. *J. Biol. Chem.* 264:18859–18862). The fibrinogen-GP IIb/IIIa binding sites recognize RGDX sequences in the fibrinogen α chains and an LGGAKQAGDV sequence on the γ chains (Bennett, J. S. et al. 1988. *J. Biol. Chem.* 263:12948–12953). Potential competing peptides of RGDS and peptides including the γ sequence LGGAKQAGDV were found to be effective antagonists of platelet aggregation (Hawiger, J. et al. 1989. *Biochemistry* 28:2909–2914). Anti-GP IIb/IIIa antibodies such as c7E3 Fab (Coller, B. S. 1997. *J. Clin. Invest.* 99:1467–1471; Coller, B. S. 1997. *Thromb. Haemost.* 78:730–735) and LJ-CP8 (Niiya, K. et al. 1987. *Blood* 70:475–483) are also potent inhibitors of fibrinogen binding to this glycoprotein complex in activated platelets.

Early studies of the cellular thrombin receptor indicated that more than one species exists in platelets (Greco, N. J. and G. A. Jamieson. 1991. *PSEBM* 198:792–799; Harmon, J. T. and G. A. Jamieson. 1986. *J. Biol. Chem.* 261:15928–15933). The first cellular thrombin receptor cloned and sequenced was PAR-1 (Vu, T-K. H. et al. 1991. *Cell* 64:1057–1068). Human platelets respond to PAR-1 and a second minor receptor PAR-4 (Kahn, M. L. et al. 1998. *Nature* 394:690–694) while the recently cloned PAR-3 is either absent on human platelets or present in trace amounts (Ishihara, H. et al. 1997. *Nature* 386:502–506). Mouse platelets respond to α-thrombin primarily through PAR-3 and secondarily through PAR4, with no involvement of PAR-1 (Vu, T-K. H. et al. 1991. *Cell* 64:1057–1068). Another platelet membrane protein, GP Ib, may also function at least in part as a thrombin receptor (Greco, N. J. and G. A. Jamieson. 1991. *PSEBM* 198:792–799; Harmon, J. T. and G. A. Jamieson. 1986. *J. Biol. Chem.* 261:15928–15933; Clemetson, K. J. 1995. *Thromb. Haemost.* 74:111–116; Greco, N. J. et al. 1996. *Biochemistry* 35:915). A major role of GP Ib, complexed with GPIX, is the specific interaction with subendothelium-bound von Willebrand factor (vWF) under high shear rates to facilitate platelet adhesion to injured vascular walls (Ruggeri, Z. M. 1994. *Semin. Hematol.* 31:229–239). The expression on the plasma membrane of the vWF receptor, GP Ib, requires the stable expression of GP Ibβ, GP Ibα, and GPIX (Lopez, J. A. et al. 1991. *J. Biol. Chem.* 267:12851–12859). The GP Ib-IX complex associates with the cytoskeletal actin binding protein (ABP) via the cytoplasmic domain of GP Ibα (Andrews, R. K. and J. E. B. Fox. 1992. *J. Biol. Chem.* 267:18605–18611; Cunningham, J. G. et al. 1996. *J. Biol. Chem.* 271:11581–11587). This GP Ibα-ABP association is initiated by the binding of vWF to GP Ib and appears to be linked to vWF-induced transmembrane signaling (Cunningham, J. G. et al. 1996. *J. Biol. Chem.* 271:11581–11587). Signal transduction appears to be regulated at least in part by one form of the 14-3-3 zeta protein (Du, X. et al. 1996. *J. Biol. Chem.* 271:7362–7367) and its association with the GP Ib-IX-V complex (Andrews, R. K. et al. 1998. *Biochemistry* 37:638–647). The GP Ib receptor also possessed a thrombin binding site that may respond to lower concentrations of thrombin than required to activate the PARs (Greco, N. J. and G. A. Jamieson. 1991. *PSEBM* 198:792–799; Harmon, J. T. and G. A. Jamieson. 1986. *J. Biol. Chem.* 261:15928–15933). The GP Ib-thrombin complex may prime the activation of PAR-1 as the thrombin levels rise (Greco, N. J. and G. A. Jamieson. 1991. *PSEBM* 198:792–799; Clemetson, K. J. 1995. *Thromb. Haemost.* 74:111–116).

The physiologic functions of the three purported platelet thrombin receptors (PAR-1, PAR-4 and GP Ib) have not yet been clearly defined. A functional role for PAR-1 in α-thrombin-induced platelet aggregation has been shown in vitro (Vu, T-K. H. et al. 1991. *Cell* 64:1057–1068). However, no comparable responses have yet been described for PAR-4 or GP Ib using a natural thrombin agonist.

SUMMARY OF THE INVENTION

An object of the present invention is a method for screening for anti-thrombotic/anti-platelet activity which comprises contacting platelets in vitro with a compound to be tested for potential anti-thrombotic/anti-platelet activity and monitoring the ability of the compound to inhibit thrombin-induced platelet aggregation through inhibition of GP Ib, PAR-1 or PAR-4 pathways, wherein the ability to inhibit the GP Ib, PAR-1 or PAR-4 pathway is indicative of antithrombotic/anti-platelet activity of the compound.

DETAILED DESCRIPTION OF THE INVENTION

A second α-thrombin-induced platelet-activating pathway, dependent on the activity of GP Ib, has been identified. The activity of this receptor is unique from that of PAR-1 and PAR-4. In addition, human platelets have also now been found to respond to γ-thrombin, an autoproteolytic product of α-thrombin, through activation of PAR-4. Co-activation of the GP Ib, PAR-1 and PAR-4 pathways was shown to result in a synergistic effect. Therefore, new strategies for antithrombotic/anti-platelet therapy can be developed based on the identification of agents that interact with GP Ib and PAR-4 as well as PAR-1. Agents that bind to the active thrombin forms or to the GP Ib and/or PAR-4 receptors or that affect thrombin binding of these receptors, can be screened in the present invention. Identification of new compounds with this screening assay will result in identification of potential new anti-thrombotic/anti-platelet drugs for use in animals, including humans.

Studies were performed to examine the role of GP Ib as a functional thrombin receptor. Platelet aggregation assays were performed employing various known inhibitors of thrombin receptors in the presence of the platelet aggregation inducers α-thrombin, γ-thrombin, the PAR-1 thrombin receptor activating peptide (TRAP-1), or the PAR-4 thrombin receptor activating peptide (TRAP-4). α-Thrombin (0.05 to 0.1 U/ml) and TRAP-1 induced platelet aggregation with similar kinetics. An equivalent amount of γ-thrombin (10 to 20 nM, comparable to the activity of 0.05 to 0.1 U/ml α-thrombin) induced platelet aggregation with distinctly slower kinetics but to an eventual similar level, as did TRAP-4. Platelets that had been preincubated with an anti-PAR-1 antibody (either a polyclonal antibody that recognized the sequence LLRNPNDKYEPF or the monoclonal antibody ATAP-2) or treated with the chemically defined PAR-1 inhibitor, SCH203099, exhibited a delayed aggregation profile relative to controls when stimulated with α-thrombin, but ultimately reached a similar level of aggregation. SCH203099 at a concentration of 5 to 10 μM did not inhibit platelet activation that was induced by 1 mM TRAP-4 or 10 to 30 nM γ-thrombin, but completely inhibited TRAP-1-induced aggregation. These data indicate that PAR-1 is not functional in the presence of the anti-PAR-1 drug SCH203099. The α-thrombin response observed with platelets pre-incubated with SCH203099 or ATAP-2 cannot be explained by displacement of the antibody/drug but instead by interaction of another receptor. PAR-4 is not the likely receptor as it is known to be insensitive to the low levels of α-thrombin employed in this study (Kahn, M. L. et al. 1998. *Nature* 394:690–694; Xu, W. -F., et al. 1998. *Proc. Natl. Acad. Sci. USA* 95:6642–6646). Therefore, GP Ib is the likely candidate.

The proof of the role of GP Ib as a functional thrombin receptor was provided by platelet aggregation studies where the anti-GP Ib antibody, LJ Ib-10, was employed. This antibody is known to selectively bind to the thrombin binding site. When platelets were incubated with the PAR-1 inhibitors SCH203099, the GP Ib antibody was still shown to have the ability to inhibit α-thrombin-induced platelet aggregation. In addition, these data demonstrated that thrombin binding to GP Ib was necessary for the response.

The presence of three distinct thrombin receptors on human platelets was shown in experiments with combinations of inhibitors and PAR-4 desensitization. Platelets treated with SCH203099 (7.5 μM) plus ATAP-2 (50 μg/ml) have the PAR-1 receptor blocked at two levels, the tethered ligand and the PAR-1 receptor site for the tethered ligand. These platelets still responded to α-thrombin after a delay period suggesting the presence of another receptor. Platelets pre-incubated for 1 hour with 350 to 700 μM TRAP-4 could not be activated by subsequent additions of 10 nM γ-thrombin or TRAP-4 at mM concentrations. In contrast, control platelets and platelets treated with SCH203099 plus ATAP-2 that were pre-incubated with TRAP-4 still aggregated upon addition of α-thrombin. This evidence indicates that TRAP-4 and γ-thrombin activate PAR-4 while α-thrombin activates PAR-1 and a third receptor, GP Ib. The delay in aggregation can be explained by the time required for the generation of polymerizing fibrin which would participate in platelet aggregation. This alternative α-thrombin pathway would be obscured normally by the rapid acting PAR-1 pathway.

The requirement of GP Ib for polymerizing fibrin was defined in a series of studies where results were compared with thrombin plus fibrinogen added to platelets versus platelets added to polymerizing fibrin. Washed platelets (50 μl) as a 10× concentrate were added to 0.05 to 0.1 U/ml α-thrombin plus fibrinogen pre-incubated for 2 minutes (polymerizing fibrin) in 430 μl buffer. The kinetics of aggregation with thrombin plus polymerizing fibrin was essentially the same as that seen with thrombin plus fibrinogen added simultaneously to platelets. Aggregation in the presence of polymerizing fibrin was not affected significantly by RGDS (fibrinogen competing peptide). In contrast, the rapid onset α-thrombin-induced PAR-1 pathway was inhibited by the fibrinogen competing peptide RGDS for the first few minutes, a time sufficient for the generation of polymerizing fibrin. Aggregation then ensued via the GP Ib pathway thus overriding the RGDS inhibition. The addition of GPRP along with RGDS completely blocked platelet aggregation while addition of GPRP alone had no significant effect on α-thrombin-induced aggregation. A recombinant mutant fibrinogen (γ407), which lacks the AGDV sequence in the γ-chain required for GP IIb/IIIa-fibrinogen interactions, still supported α-thrombin-induced aggregation as did recombinant wild-type fibrinogen. Aggregation via the PAR-1 pathway was again initially blocked by the addition of RGDS when γ407 replaced normal fibrinogen, until γ407 began to polymerize. Residual adhering/endogenous fibrinogen did not account for the observed aggregation since none occurred in the presence of RGDS without added fibrinogen. Aggregation occurred with polymerizing γ407 via the GP Ib pathway even in the presence of RGDS, although at a reduced level.

RGDS also completely blocked aggregation induced by U46619 and ADP, two agonists that cannot generate polymerizing fibrin as can α-thrombin. When the thrombin inhibitor hirudin was added to platelets (1 to 2 U/ml) followed by addition of thrombin plus fibrinogen, aggregation was completely inhibited. If the inhibitor was added 2 minutes after fibrinogen was pre-incubated with thrombin, and then platelets added 30 seconds later, hirudin continued to prevent aggregation completely, indicating that polymerizing fibrin alone cannot account for the observed aggregations as platelet "trapping".

Further studies were conducted to distinguish between polymerizing fibrin-dependent platelet aggregation versus platelet trapping. True platelet aggregation involves signal transduction, second messenger formation with subsequent mobilization of internal calcium stores and the platelet release reaction. Platelet trapping, in contrast, by polymerizing fibrin would not involve any of these secondary responses. Control and SCH203099-treated platelets were pre-loaded with Fura-2 and then shown to mobilize internal calcium in response to α-thrombin while only control platelets responded to TRAP-1. The mobilization of internal calcium was delayed in the SCH203099-treated platelets as compared to controls, in the same manner that was seen for kinetics of platelet aggregation. The platelet release reaction was monitored by release of dense granule ATP. Here the release reaction was followed simultaneously with aggregation. Drug-treated platelets were shown to aggregate under conditions dependent on polymerizing fibrin with equal amounts of ATP release to the corresponding control samples that can aggregate independent of polymerizing fibrin. However, conditions that induced platelet adhesion/polymerizing fibrin-trapping were not associated with any ATP release.

The serine protease inhibitor, AEBSF, completely inhibited aggregation when added to thrombin prior to the addition of fibrinogen and platelets. However, AEBSF did not inhibit aggregation when added after the formation of the thrombin-fibrin complex, but prior to the addition of platelets. These data suggest that thrombin-induced aggregation via the GP Ib pathway requires thrombin interaction with GP Ib but is independent of proteolytic activity at the receptor site as long as polymerizing fibrin is present. AEBSF blocks the catalytic site, but not the GP Ib-binding site of thrombin. Platelets were treated under identical conditions with AEBSF plus the thrombin substrate CBS 34.47 (7.5 µM) in order to determine if AEBSF remains active in the presence of the polymerizing fibrin-thrombin complex. After 5 minutes incubation, the platelets were pelleted in a microcentrifuge for 4 minutes at 14,000 rpm and the generation of product was monitored at 405 nm. AEBSF inhibited thrombin activity in excess of 90%.

Significant synergistic responses were observed with suboptimal doses of α-thrombin plus TRAP-4, as well as α-thrombin plus γ-thrombin or TRAP-1 plus TRAP-4. In all cases, the sum of the aggregation induced by the individual agonists at suboptimal concentrations varied between 0 and 15% (agonist concentrations varied between 0.01 and 0.005 U/ml for α-thrombin; 0.1 to 2 nM for γ-thrombin; 0.38 to 0.76 µM for TRAP-1; 175 to 350 µM for TRAP-4). The low dose of α-thrombin employed was below the level required to function at PAR-1 or PAR-4 but adequate to activate GP Ib. TRAP-4 and γ-thrombin appeared to function only at PAR-4. To demonstrate the synergy between GP Ib and PAR-4 and to exclude a role for PAR1, platelets were incubated with SCH203099 to inactivate PAR1. The SCH203099-treated platelets had a significant response with low dose α-thrombin plus TRAP-4 but the synergistic response was totally abolished in the presence of Fab-10.

These data indicate that human platelets responded to α-thrombin via PAR-1 and GP Ib receptors through mechanisms that are distinct in vitro. Therefore, the mechanisms in vivo would also be distinct. The second PAR receptor, PAR-4 did not appear to respond to physiologic levels of α-thrombin but may be responsive to in vivo generated γ-thrombin based on the in vitro data. The synergistic effect of minimally activated thrombin receptors has significant implications for in vivo thrombotic events. Multiple platelet thrombin receptors may reflect the physiological requirement to respond differentially to varying concentrations of α, β, and γ-thrombins and/or to different presentations of thrombin complexed with other proteins. The presence of the GP Ib receptor as a functional thrombin receptor, independent of fibrinogen, along with the synergy shown with the PAR-4 receptor, explains why anti-α-thrombin/anti-platelet regimens fail to completely inhibit thrombosis and restenosis in cardiac patients.

Experiments were performed to demonstrate further that the three thrombins function differentially at the three platelet thrombin receptors and respond differently to thrombin inhibitors. At 0.1 to 10 nM levels of the thrombins, PAR-4 was only activated by γ-thrombin while GP Ib and PAR-1 are insensitive to γ-thrombin but both respond to α-thrombin. β-thrombin was more selective for PAR-4. The interaction of γ-thrombin with PAR-4 was inhibited stoichiometrically by histone-1 while α-thrombin and α-thrombin and their receptors were insensitive to histone-1. The three thrombin species displayed different sensitivities to heparin as well. Further, γ-thrombin was totally insensitive to hirudin while α-thrombin and β-thrombin were completely inhibited by this compound. These data clearly demonstrated the differential responses of the thrombin receptors to the three forms of thrombin.

The present invention is a screening assay for identifying agents capable of inhibiting platelet aggregation through interactions with α-, β-, or γ-thrombin, and/or the thrombin receptors, GP Ib, PAR-1 or PAR-4. The assay includes analysis of α-thrombin/PAR-1 interactions and compound or inhibitor/α-thrombin interactions for comparative purposes only since these interactions are generally known to occur. A method is provided for screening for antithrombotic/anti-platelet activity which comprises contacting platelets in vitro with a compound to be tested for potential anti-thrombotic/anti-platelet activity and monitoring the ability of the compound to inhibit thrombin-induced platelet aggregation through modulation of GP Ib, PAR-1 or PAR-4 receptor binding, and/or through selective inhibition of α-, β-, or γ-thrombin interactions, wherein the ability to inhibit platelet aggregation via inhibition of binding to the GP Ib, PAR-1 or PAR-4 receptors or by blocking specific intracellular pathways linked to these receptors is indicative of antithrombotic/anti-platelet activity of the compound. The methods for monitoring inhibition of thrombin binding to the respective receptors and/or the inhibitor binding selectively to different thrombins are provided above as described in platelet aggregation experiments. Other methods for monitoring thrombin binding inhibition may be developed in the future. This method provides for development of new antithrombotic/anti-platelet compounds for use therapeutically. One of skill would understand how to use agents identified as inhibitors of GP Ib based on the knowledge general to the art of drug development.

The following non-limiting examples are provided to further illustrate the invention.

EXAMPLES

Example 1

Platelet Preparation

Blood was drawn by venopuncture into plastic tubes that contained 1/10 volume 3.8% citrate and platelet-rich plasma (PRP) was prepared in accordance with known techniques (Soslau, G. and J. Giles. 1982. *Thrombos. Res.* 26:443–455). Blood samples were obtained from healthy donors who were medication free. Washed platelets were prepared from the PRP by known methods (Basheer, A. R. et al. 1995. *Biochim. Biophys. Acta* 1250:97–109). Briefly, PRP was diluted with 3 volumes of 100 nM citrate buffer (pH 6.0) plus 1 to 2 volumes of hepes Tyrode's buffer (pH 7.4), final volume of 50 ml, and resuspended in hepes Tyrode's buffer with 1 mg/ml dextrose plus 1 mg/ml bovine serum albumin at $2 \times 10^6/\mu l$ to $3 \times 10^6/\mu l$ (a 10× normal concentration).

Example 2

Platelet Aggregation

Platelet aggregations were performed on a dual-channel Chronolog lumi aggregometer (Chronolog Corp., Havertown, Pa.) by known methods (Soslau, G. et al. 1988. *Biochem. Biophys. Res. Commun.* 15:909–916). Aggregations were conducted with 480 µl washed platelets or a 50 µl sample of the concentrated platelets added to 430 µl hepes Tyrode's buffer with a final platelet count of $2 \times 10^5/\mu l$ to $3 \times 10^5/\mu l$. Agonists and antagonists were added at various concentrations.

Example 3

Calcium Mobilization

The mobilization of internal stores of calcium, $[Ca^{+2}]_i$, was monitored with a Hitachi F-2000 fluorescence spectrophotometer in the presence of extracellular EGTA to chelate the extracellular $Ca^{+2}$ (Soslau, G. et al. 1995. *Biochim. Biophys. Acta* 1268:73–80). Platelets, as PRP, were preloaded with 1 µM Fura-2 AM for 45 to 60 minutes and then washed and resuspended in hepes Tyrode's buffer at a concentration of 10×. Samples were incubated at room temperature with or without 10 μM SCH 203099 for one hour prior to analysis. A 50 μl sample of platelets was added to 430 μl hepes Tyrode's buffer in a quartz microcuvette with a 4.5 mm path length with stirring at 37° C. Agonists were added through an injection port at various concentrations. Excitation wavelengths were 340 nm and 380 nm and emission was measured at 505 nm. Calibration and conversion of raw data were performed.

Example 4

ATP Release

The platelet release reaction was monitored simultaneously in some experiments with aggregation per known techniques (Soslau, G. and J. Parker. 1992. *Thromb. Res.* 66:15–21). The release of dense granule ATP from aggregating platelets was detected as light emission in the Chronolog lumi-aggregometer produced by the reaction of ATP with luciferin catalyzed by luficerase (chrono-lume).

What is claimed is:

1. A method for screening for compounds having anti-thrombotic/anti-platelet activity comprising:

a) contacting platelets in vitro with a compound to be tested for potential anti-thrombotic/anti-platelet activity; and b) monitoring activity of said compound to inhibit thrombin-induced platelet aggregation through inhibition of GP Ib, PAR-1 and PAR-4 receptor binding, wherein activity as an inhibitor of GP Ib and PAR-1 or PAR-4 binding is indicative of anti-thrombotic/anti-platelet activity of said compound.

2. A method for screening for compounds having anti-thrombotic/anti-platelet activity comprising:

a) contacting platelets in vitro with a compound to be tested for potential anti-thrombotic/anti-platelet activity; and b) monitoring activity of said compound to inhibit thrombin-induced platelet aggregation through inhibition of α-thrombin, β-thrombin, and γ-thrombin pathways wherein activity as an inhibitor of any of α-thxombin, β-thrombin, or γ-thrombin pathways is indicative of anti-thrombotic/anti-platelet activity of said compound.

* * * * *